US010681910B2

(12) United States Patent
Wen et al.

(10) Patent No.: US 10,681,910 B2
(45) Date of Patent: Jun. 16, 2020

(54) ANTIMICROBIAL WASH

(71) Applicant: Medtronic Xomed, Inc., Jacksonville, FL (US)

(72) Inventors: Jie Wen, St. Johns, FL (US); Dana A. Oliver, Jacksonville, FL (US)

(73) Assignee: MEDTRONIC XOMED, INC., Jacksonville, FL (US)

(*) Notice: Subject to any disclaimer, the term of this patent is extended or adjusted under 35 U.S.C. 154(b) by 0 days.

(21) Appl. No.: 15/837,711

(22) Filed: Dec. 11, 2017

(65) Prior Publication Data

US 2018/0110229 A1 Apr. 26, 2018

Related U.S. Application Data

(62) Division of application No. 14/328,841, filed on Jul. 11, 2014, now Pat. No. 9,484,604.

(51) Int. Cl.
*A01N 47/44* (2006.01)
*A61Q 17/00* (2006.01)
*A61K 8/84* (2006.01)
*A01N 25/00* (2006.01)
*A61K 9/00* (2006.01)
*A61K 31/785* (2006.01)
*A61L 2/00* (2006.01)
*A61L 9/00* (2006.01)

(52) U.S. Cl.
CPC .......... *A01N 47/44* (2013.01); *A01N 25/00* (2013.01); *A61K 8/84* (2013.01); *A61K 9/0043* (2013.01); *A61K 9/0046* (2013.01); *A61K 31/785* (2013.01); *A61L 2/00* (2013.01); *A61L 2/0005* (2013.01); *A61L 9/00* (2013.01); *A61Q 17/005* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 4,403,078 A | 9/1983 | McCoy et al. | |
| 4,558,159 A | 12/1985 | McCoy et al. | |
| 4,891,423 A | 1/1990 | Stockel | |
| 5,167,950 A | 12/1992 | Lins | |
| 5,498,416 A | 3/1996 | Carsenti-Etesse et al. | |
| 5,741,886 A | 4/1998 | Stockel et al. | |
| 5,942,218 A | 8/1999 | Kirschner et al. | |
| 7,772,284 B2 | 8/2010 | Labib et al. | |
| 7,993,675 B2 | 8/2011 | Oliver et al. | |
| 8,653,319 B2 | 2/2014 | Amery et al. | |
| 2005/0101511 A1 | 5/2005 | Zocchi | |
| 2007/0264353 A1 | 11/2007 | Myntti et al. | |
| 2007/0282008 A1 | 12/2007 | Mason | |
| 2010/0204181 A1 | 8/2010 | Stroman et al. | |
| 2011/0245757 A1 | 10/2011 | Myntti et al. | |
| 2013/0171224 A1 | 7/2013 | Percival et al. | |
| 2015/0164829 A1 | 6/2015 | Twomey et al. | |

FOREIGN PATENT DOCUMENTS

| | | |
|---|---|---|
| EP | 2 156 853 A1 | 2/2010 |
| GB | 720268 A | 1/1954 |
| GB | 2 338 649 A | 12/1999 |
| WO | WO97/00076 | 1/1997 |
| WO | WO 2003004013 A1 | 1/2003 |
| WO | WO2009/117299 A2 | 9/2009 |
| WO | WO2010/083589 A1 | 7/2010 |
| WO | WO 2012/085068 A1 | 6/2012 |
| WO | WO 2013016255 A1 | 1/2013 |

OTHER PUBLICATIONS

Priority U.S. Appl. No. 14/328,841, filed Jul. 11, 2014 (now allowed).
International Application No. PCT/US2015/039283, International Search Report and Written Opinion dated Sep. 17, 2015.
"RE: Premarket Notification Exemption Letter for Ethmoid Sinus Spacer", Acclarent, Inc., 8 pages (Apr. 16, 2007).
Benninger et al., "Adult chronic rhinosinusitis: Definitions, diagnosis, epidemiology, and pathophysiology", Otolaryngol Head Neck Surg 129 (3 suppl): S1-S32 (2003).
Nadel et al., "Endoscopically guided cultures in chronic sinusitis", Am J Rhinol 12:233-241 (1998).
Stepanovic et al.,"A modified microliter-plate test for quantification of staphylococcal biofilm formation", J Microbiol Methods 40:175-179 (2000).
Gotz, "*Staphylococcus* and biofilms", Mol Microbiol 43:1367-1378 (2002).
Kalid et al., Physiologic Alterations in the Murine Model After Nasal Fungal Antigenic Exposure, Otolaryngology 139:695-701 (2008).
Bradbury S. et al., Prontosan® made easy, Wounds International, vol. 2, Issue 2, 6 pages (May 2011).
Desrosiers, M. M.D. et al., Methods for removing bacterial biofilms: In vitro study using clinical chronic rhinosinusitis specimens, American Journal of Rhinology, vol. 21, No. 5, Sep.-Oct. 2007.
ECHA, Background Document to RAC Opinion on PHMB, 77 pages (2011).
PHMB and its potential contribution to wound management, 15 pages (2010).
EPA, Reregistration Eligibility Decision for PHMN, 98 pages (2004).
Prontosan A real knockout in wound cleaning, 1 page (downloaded May 29, 2013).
O'Malley, L.P. et al., Microbial degradation of the biocide polyhexamethylene biguanide: isolation and characterization of enrichment consortia and determination of degradation by measurement of stable isotope incorporation into DNA, Journal of Applied Microbiology, vol. 103, pp. 1158-1169 (2007).

(Continued)

*Primary Examiner* — Melissa L Fisher
(74) *Attorney, Agent, or Firm* — Patterson Thuente Pedersen, P.A.

(57) ABSTRACT

A method for detaching, removing or otherwise disrupting bacteria or biofilm by applying with pressure an antimicrobial wash. The antimicrobial wash contains a biguanide compound or mixtures thereof.

9 Claims, No Drawings

(56) References Cited

OTHER PUBLICATIONS

Schipor, I. M.D., Quantification of ciliary beat frequency in sinonasal epithelial cells using differential interference contrast microscopy and high-speed digital video imaging, American Journal of Rhinology, vol. 20, No. 1, pp. 124-127 and 1 copyright information sheet (Jan.-Feb. 2006).

Schipor, I. MD, et al., Quantification of ciliary beat frequency in sinonasal epithelial cells using differential interference contrast microscopy and high-speed digital video imaging, American Journal of Rhinology, January-February, vol. 20, No. 1, pp. 124-127, Copyright page (2006).

Shah, Chirag B.,Ph.D., Rish Assessment of Kendall™ AMD Antimicrobial Foam Dressings Containing (0.5%) PHMB, Bioscience and Materials R&D, Covidien, Mansfield, MA, 4 pages (2009).

Suprasorb® X + PHMB, Antimicrobial HydroBalance Wound Dressing, p. 45 (2010).

Hadaway, L., M.Ed., RN, BC, CRNI, Polyhexamethylene Biguanide Dressing—Another Promising Tool to Reduce Catheter-related Bloodstream Infection, Java, vol. 15, No. 4, pp. 203-205 (2010).

Moore G. et al., Problems associated with traditional hygiene swabbing: the need for in-house standardization, The Society of Applied Microbiology, Journal of Applied Microbiology, vol. 103, pp. 1090-1103 (2007).

Ferguson et al., "Demonstration of Biofilm in Human Bacterial Chronic Rhinosinusitis", Am J Rhinol, 5: 19, pp. 452-457 (2005).

Leicth et al., The effects of ethanol on mucociliary clearance, *Alcohol Clin Exp Res.* 9(3):277-80 (1985).

Bernstein, Use of benzalkonium chloride as a preservative for nasal formulations a safety concern? A cautionary note based on compromised mucociliary transport, J Allergy Clin Immunol 105:39-44 (2000).

Gosepath et al., Topical antibiotic, antifungal, and antiseptic solutions decrease ciliary activity in nasal respiratory cells, Am J Rhinol, 16(1):25-31 (2002).

Riechelmann et al., Nasal toxicity of benzalkonium chloride, Am J Rhino, 18(5):291-99 (2004).

Chennupati et al., Effects of an LL-37-derived antimicrobial peptide in an animal model of biofilm *Pseudomonas* sinusitis, Am J Rhino, 23:46-51 (2009).

Editorial, The role of topical therapies in the treatment of Chronic Rhinosinusitis, Braz J Otorhinolaryngol, 77(6):680-1 (2011).

Atkins, NeilMed's SinuSurf Additive Causes Loss of Sense of Smell (2011; web page at www.texassinuscenter.com/neilmeds-sinusurf-additive-causes-loss-of-sense-of-smell/).

Rosen et al., Surfactants in the management of rhinopathologies, A J Rhino, 27(3):177-80 (2013).

Kim et al., Betadine has a ciliotoxic effect on ciliated human respiratory cells, J Laryngol Otol. 129 Suppl 1:S45-50 (2015).

Presentation by Chiu entitled Management of the Recalcitrant FESS Patient (2015).

Dimova et al, Safety assessment of 3-methoxyquercetin as an antirhinoviral compound for nasal administration: effect on ciliary beat frequency, Int J Pharmaceutics 263, pp. 95-103 (2003).

UPMC Patient care instructions at:www.upmc.com/patients-visitors/education/otolaryngology/pages/home-care-instructions-after-sinus-surgery.aspx.

Meyer, "Approaches to prevention removal and killing of biofilms", International Biodeterioration & Biodegradation, 51, pp. 249-253 (2003).

Horrocks, "Prontosan® Wound Irrigation and Gel: management of chronic wounds", British Journal of Nursing, 15(22), pp. 1222-1228 (2006).

Braun, Prontosan® Wound Irrigation Solution and Gel with Polyhexanide (PHMB) and Betaine (surfactant), https://www.bbraunusa.com/documents/Nanosites/Prontosan-Applications-in-Use-Booklet-10-18-10.pdf, accessed Sep. 30, 2015.

Braun, "Prontosan® Wound Irrigation Solution", https://www.bbraun.usa.com/documents/ProntosanWound_Gel_40mL.pdf, accessed Sep. 30, 2015.

Extended European Search Report for Application No./Patent No. EP 17 19 1482 dated Nov. 27, 2017, 12 pages.

Mills, P.C. et al., "Ototoxicity and tolerance assessment of a TrisEDTA and polyhexamethylene biguanide ear flush formulation in dogs", Journal vet. Pharmacol. Therap., 28, pp. 391-397 (2005).

Examination Report for counterpart European Application No. 15745299.6, dated Apr. 8, 2019 (4 pages).

Çankaya et al., "Effects of topical chlorhexidine applied to the rabbit nasal mucosa", Auris, Nasus, Larynx 30, Jan. 1, 2003, pp. 65-69, Retrieved from the Internet at URL: https://www.aurisnasuslarynx.com/article/S0385-8146(02)00102-5/pdf.

ANTIMICROBIAL WASH

CROSS-REFERENCE TO RELATED APPLICATION

This application is a divisional of and claims priority from U.S. patent application Ser. No. 14/328,841, filed Jul. 11, 2014 (now allowed), the disclosure of which is incorporated herein by reference.

FIELD OF THE INVENTION

This invention relates to biofilm removal.

BACKGROUND

Biofilms form when bacteria interact with a surface to form polymeric films (sometimes referred to as exopolysaccharide or extracellular polysaccharide (EPS) polymers) that, coat the surface and provide a living colony for further bacterial proliferation. Bacteria lodged in biofilms are much more difficult to remove or kill than bacteria in a planktonic (suspended) state, and are resistant to many antibiotics and biocides.

When present on human tissues, bacteria and biofilms can cause chronic conditions from which many persons today suffer. Such conditions include rhinosinusitis, where biofilms are attached within the nasal passages and sinuses. Implants or surgical devices may also be enclosed or encased within biofilms, which may lessen the implant's or surgical device's effectiveness.

SUMMARY OF THE INVENTION

It would be desirable to remove or disrupt biofilms on tissue or implant devices so that remaining bacteria may more effectively be attacked by antibiotics or by the body's own natural defenses.

The present invention provides, in one aspect, a method for removing biofilm comprising:
 applying with pressure an antimicrobial wash comprising a biguanide compound or mixtures thereof to a biofilm attached or adhered to a surface of a human or animal tissue, or on an implant device; and
 detaching, removing or otherwise disrupting at least a part of the biofilm.

The invention provides, in another aspect, a method for treating rhinosinusitis and other bacterial sinus conditions, which method comprises:
 applying with pressure an antimicrobial wash comprising a biguanide compound or mixtures thereof to a treatment site within a nasal or sinus cavity; and
 detaching, removing or otherwise disrupting bacteria or tissue within the nasal or sinus cavity to provide a greater than 1-log order reduction in one or more of *Staphylococcus aureus, Pseudomonas aeruginosa, Staphylococcus epidermidis, Escherichia coli Staphylococcus pneumonia, Haemophilus influenzae* or *Moraxella catarrhalis* bacteria.

The invention provides, in another aspect, a method for treating otitis media and other bacterial ear conditions, which method comprises:
 applying with pressure an antimicrobial wash comprising a biguanide compound or mixtures thereof to a treatment site within an ear; and
 detaching, removing or otherwise disrupting bacteria or tissue within the ear to provide a greater than 1-log order reduction in one or more of *Staphylococcus aureus, Pseudomonas aeruginosa, Staphylococcus epidermidis, Escherichia coli Staphylococcus pneumonia, Haemophilus influenzae* or *Moraxella catarrhalis* bacteria.

The invention provides, in another aspect, a kit for treating bacterial conditions comprising a device that can apply solution with pressure; the device containing an antimicrobial solution comprising a biguanide solution and printed instructions describing proper use of the kit.

The invention provides, in another aspect, an apparatus for treating bacterial conditions comprising:
 a spray device containing an antimicrobial solution comprising a biguanide solution.
 the spray device capable of applying the antimicrobial solution with pressure.

The invention provides, in yet another aspect, an apparatus for treating bacterial conditions comprising:
 a spray device containing an antimicrobial solution comprising a biguanide solution,
 wherein the biguanide solution is non-ciliotoxic.

The disclosed method and composition may be used in ear, nose and throat applications such as treatment of otitis media and cholesteatoma.

DETAILED DESCRIPTION

The following detailed description describes certain embodiments and is not to be taken in a limiting sense. All weights, amounts and ratios herein are by weight, unless otherwise specifically noted. The terms shown below have the following meanings:

The term "antimicrobial" when used in reference to a substance means that the substance can kill, significantly inhibit, reduce or control the growth of microbes, for example bacteria such as *Staphylococcus aureus, Streptococcus epidermis, Staphylococcus pneumonia, Haemophilus influenza, Moraxella catarrhalis, Pseudomonas aeruginosa, Escherichia coli,* or other bacteria and *Aspergillus, Mucor, Alternaria, Bipolaris, Curvularia* or other fungi implicated in the etiology of rhinosinusitis, otitis media, or chronic wounds.

The terms "attached" and "adhered" when used in reference to bacteria, a biofilm and a surface mean that the bacteria and biofilm are established on and at least partially coats or covers the surface, and has some resistance to removal from the surface. As the nature of this relationship is complex and poorly understood, no particular mechanism of attachment or adherence is intended by such usage.

The term "adhesion" when used in reference to tissue refers to the sticking together of a material to tissues or tissue to tissue with which it is in intimate contact for extended periods or tissue that connects opposing tissues or prosthetic materials across a normally open space.

The term "biodegradable" when used in reference to a substance means that the substance will degrade or erode in vivo to form smaller chemical species. Such degradation process may be enzymatic, chemical or physical.

The term "biofilm" means a community of bacteria attached to a surface, with the organisms in the community being contained within an extracellular polymeric (e.g. polysaccharide) substance (EPS) matrix produced by the bacteria.

The term "bioresorbable" when used in reference to a substance means that the substance is capable of being absorbed by the body.

The terms "detaching", "removing" and "disrupting" when used in reference to bacteria or a biofilm attached or adhered to a surface mean that at least a significant amount of the bacteria or biofilm initially present on the surface no longer is attached or adhered to the surface. No particular mechanism of detachment, removal or disruption is intended by such usage.

The term "debride" when used in reference to devitalized tissue attached within a treatment site refers to cutting away or otherwise excising the tissue so that it is no longer attached. No particular mechanism of debridement is intended by such usage.

The term "devitalized" when used in reference to tissue means tissue that is sufficiently devoid of life so that it will not heal if left untreated.

The term "implant device" means implantable and implanted devices, including prosthetic devices.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx, and to objects, devices or articles (e.g., prostheses, packing or stents) that may be placed within a nasal or sinus cavity.

The term "otitis media" refers to a spectrum of diseases in which fluid (effusion) is present in the middle ear space. A middle ear infection may exhibit symptoms of ear ache, temporary hearing loss, or pus drainage from the infected ear.

The term "polymeric sealant" means that the sealant is either formed from a synthetic crosslinked or uncross linked polymer or from a natural polymer (e.g. a polysaccharide) which is crosslinked or uncrosslinked.

The term "residence time" when used in reference to a polymeric sealant at a treatment site means the time period during which the sealant remains in place in vivo under gross observation.

The disclosed antimicrobial wash is an aqueous solution containing a biguanide compound. The antimicrobial wash may be applied to a desired treatment site with pressure or other techniques to detach, remove or otherwise disrupt at least a part of bacteria or a biofilm attached or adhered to at least a portion of tissue (e.g., nasal or sinus cavities, or ear) or implant devices. The antimicrobial wash desirably is applied with a device or system that mechanically detaches, removes or otherwise disrupts the bacteria and biofilm. The delivery of the antimicrobial wash with sufficient fluid volume and coverage (e.g. about 50 to about 100 mL/cm$^2$), sufficient pressure (e.g. about 30,000 to about 480,000 Pascal) or both disrupts or otherwise detaches the bacteria or biofilm. While not wishing to be bound by theory, the disrupted biofilm may no longer provide protection to the microbes, thus making the microbes more susceptible to the antimicrobial wash.

The thus-disrupted biofilm can be more easily flushed, or otherwise removed from the treatment site using aspiration, lavage or other removal techniques. In other cases, the antimicrobial wash may be left in place until it can drain away or is otherwise eliminated or resorbed, or the antimicrobial wash may be allowed to stand for a suitable time (e.g., a few minutes, a few hours or longer) and then may be rinsed away using saline or another suitable liquid. Application of the antimicrobial wash and removal of dislodged or disrupted biofilm and bacteria may also be repeated as desired to ensure thorough removal of offending organisms.

In some embodiments, the antimicrobial wash may be used with sufficient pressure or other techniques to accomplish, debridement, bacterial and biofilm disruption or removal. Pressure used to deliver the antimicrobial wash to a target site desirably may be about 30,000 Pascal (4.4 psi) to about 480,000 Pascal (70 psi) or about 170,000 Pascal (25 psi) to about 340,000 Pascal (50 psi). The pressure is measured from a distance of about 2.5 mm to about 25.4 mm from the device tip to the target site. In addition, flow rates, for example, more than 1 mL/sec to about less than 20 mL/sec are desirable. In some embodiments, both pressure and flow rate may assist in debridement, biofilm disruption or both.

Exemplary devices or systems include any sprayer which can apply the antimicrobial wash with sufficient pressure. The antimicrobial wash may be applied continuously or pulsed. Commercially available sprayers or devices include PULSAVAC™ and PULSAVAC PLUS™ wound debridement systems (Zimmer, Inc.); the SONICONE™ ultrasonic wound debridement system (Misonix, Inc.); the VERSA-JET™ hydrosurgery system (Smith & Nephew, Inc.); the SPINEJET™ hydrosurgery system (HydroCision, Inc.); the RELIEVA VORTEX® 2 sinus irrigation system (Acclarent, Inc.); and the HYDRODEBRIDER™ system (Medtronic Xomed, Inc.).

The biguanide compounds preferably include a polybiguanide. Exemplary polybiguanides include polyhexamethylenebiguanide (PHMB), also known as polyhexanide and polyaminopropylbiguanide and salts thereof. Exemplary PHMB salts include polyhexamethylenebiguanide hydrochloride, polyhexamethylenebiguanide hydrobromide, polyhexamethylenebiguanide borate, polyhexamethylenebiguanide acetate, polyhexamethylenebiguanide gluconate, polyhexamethylenebiguanide sulfonate, polyhexamethylenebiguanide maleate, polyhexamethylenebiguanide ascorbate, polyhexamethylenebiguanide stearate, polyhexamethylenebiguanide tartrate, polyhexamethylenebiguanide citrate, and combinations thereof. Other suitable biguanides include, for example, chlorhexidine and octenidine.

The biguanide compound is present in the aqueous solution in an amount effective to provide antimicrobial activity (e.g., bactericidal and/or bacteriostatic activity) in the treatment site. Compositions may include about 0.005 wt % to about 0.5 wt % biguanide compound in the total solution. Preferably, the composition includes about 0.01 wt % to about 0.3 wt % and most preferably from about 0.025 wt % to about 0.2 wt % biguanide compound in total solution. The biguanide compound may provide additional anti-inflammatory benefit to the treatment site.

The polybiguanide compound desirably has a weight average molecular weight of about 1.000 to about 50,000; preferably between 2,000 to about 5,000 as determined by gel permeation chromatography. The preferred polybiguanide, PHMB, may be synthesized by polycondensation of sodium dicyanamide and hexamethylenediamine and as described for example in GB Patent No. 702,268. Other synthesis routes are described for example in U.S. Pat. Nos. 4,403,078, 4,558,159, 4,891,423 and 5,741,886.

The antimicrobial wash may be formed by mixing or dissolving the biguanide in water or a saline solution. If saline is used, the saline solution may be about 0.5 wt. % to about 3.0 wt. % sodium chloride solution. The saline solution can be hypotonic, isotonic or hypertonic. Desirably, the saline is at physiological concentration, (viz. about 0.9 wt % saline).

The antimicrobial wash preferably has the ability to cause a 90% numeric reduction (viz., at least a 1-log order reduction) or greater in a population of one or more of bacteria using the bacterial plate count procedure described below in the Examples. In other embodiments, the antimicrobial wash preferably provides greater than a 99% numeric reduction (viz., at least a 2-log order reduction), greater than a 99.9% numeric reduction (viz., at least a 3-log order reduction), greater than a 99.99% numeric reduction (viz., at least a 4-log order reduction) or greater than a 99.999% numeric reduction (viz., at least a 5-log order reduction) in a population of one or more bacteria using the bacterial plate count procedure described below in the Examples.

Compositions containing about 0.005 wt % to about 0.02 wt % biguanide preferably provide greater than a 99% numeric reduction (viz., at least a 2-log order reduction). In some embodiments, the compositions containing about 0.02 wt % to about 0.5 wt % PHMB preferably provide greater than a 99.9% numeric reduction (viz., at least a 3-log order reduction).

Desirably, the antimicrobial wash does not contain ingredients which might potentially harm tissues or structures in the nasal cavities, sinus cavities, or ear. The disclosed antimicrobial wash desirably is non or low cytotoxic with cytotoxicity scores of 0, 1, 2 or 3 as measured by guidelines of ISO10993-5, Biological Evaluation of Medical Devices—Part 5: Tests for in vitro Cytotoxicity. The disclosed antimicrobial wash is desirably also non-ciliotoxic. In other embodiments, the disclosed antimicrobial wash desirably is also non-ototoxic.

The antimicrobial wash may optionally contain a surfactant. The surfactant desirably is water-soluble and non-toxic. Exemplary surfactants are described in U.S. Pat. No. 7,993,675 B2.

The antimicrobial wash may optionally contain a lubricating or wetting agent. One preferred class of lubricants and wetting agents includes hydroxy compounds having two or more hydroxyl groups with the presence of 1,2-diol grouping being desirable. Hydroxy compounds having 2-4 carbon atoms have been found to be particularly useful lubricants. Glycerol is especially preferred. Other compounds include ethane-1,2-diol; propane-1,2-diol; butane-1,3-diol and butane-1,4-diol. Mixtures of hydroxy compounds may be employed, especially mixtures of glycerol and one or more diols. When a lubrication or wetting agent is used, it may be for example about 0.1 wt % to about 15 wt % or about 0.5 wt % to about 10 wt % of the total solution.

In some embodiments, the antimicrobial wash contains less than 0.2 wt. % surfactant and less than 1 wt % wetting or lubricating agent. Preferably, the antimicrobial wash is free or substantially free of surfactants, wetting agents or both.

The antimicrobial wash may optionally further contain other cationic ions, such as $Mg^{2+}$, $Zn^{2+}$, $K^+$, $Fe^{3+}$, $Ca^{2+}$ and the like, and anionic ions such as $CH_3COO^-$, $Br^-$, $F^-$, and the like. These ions may provide buffering capability or additional hemostatic function, or may be essential for healthy ciliary growth. The antimicrobial wash may also contain other hemostatic agents, cilia promoting agents, wound healing agents, or anti-inflammatory agents.

The disclosed antimicrobial wash may be placed in suitable sealed packaging (for example, a syringe, a vial, or pouch) made of suitable materials, (e.g. plastic or glass). In some embodiments, the antimicrobial wash may be packaged in an intravenous bag or syringe.

The antimicrobial wash may be subjected to sterilization before or after packaging. Sterilization methods that do not unduly affect the packaging or the antimicrobial wash are desirable. Sterilization methods that do not significantly change the antimicrobial wash concentration, for example, the concentration change may be within ±10% of the initial antimicrobial wash concentration before sterilization are desirable. Suitable sterilization methods include filtration, autoclave, and ionizing radiation (e.g. gamma radiation and electron bean's (E-Beam). E-beam sterilization may be performed at reduced temperatures as described in U.S. Pat. No. 8,653,319 B2 (Amery et al). E-beam or gamma sterilization may for example be used at doses in the range of about 12 to about 60 kGy.

The antimicrobial wash which may be employed in the disclosed method may also be a kit that includes a device that provides sufficient pressure (e.g., syringes or sprayers) to detach, remove or otherwise disrupt bacteria or biofilms and printed instructions describing the proper use of the kit for application to the treatment site.

To discourage bacterial recolonization and biofilm reformation, a polymeric film-forming medical sealant may optionally be applied to the treatment site. A variety of polymeric film-forming medical sealants may be used in the disclosed method. The sealant preferably is a biodegradable or bioresorbable material having a residence time in vivo from one day to a few days (e.g., 2, 3 or 4 days), weeks or months. The sealant may fee uncrosslinked, crosslinked before being applied to the treatment site, or crosslinked after application. In one embodiment, the sealant may be a viscoelastic material. In another embodiment, the sealant may harden after application. The sealant may further include other antimicrobial compounds. Exemplary sealants and exemplary antimicrobial compounds are those described in U.S. Pat. No. 7,993,675 B2. The sealant may be applied using any device such as the hydrodebrider or as disclosed in U.S. Pat. No. 7,993,675 B2. The applied sealant may fill the treated sites (e.g., nasal or sinus cavities or may be applied as a film or other conformal coating that leaves at least a partial air opening in the treated cavities. The sealant desirably adheres to natural tissues at the treatment site and resists detachment or other disruption until natural degradation or resorption of the sealant takes place. Meanwhile, recolonization or reinfection may be significantly reduced or prevented, and improved healing and reciliation may take place. The sealant may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, or the like. These advantages may arise due to a variety of mechanisms including a) inhibiting bacterial colonization, b) inhibiting the adherence of bacteria to tissue, c) reducing tissue morbidity or abscess formation, d) reducing or preventing disease recurrence (for example, specifically reducing the chronic inflammation related to bacterial toxin and EPS), e) coating and protecting tissue during healing, such as by maintenance of a moist wound which promotes platelet aggregation, or by closure of a dry wound without excessive scabrous formation, f) hemostasia, g) optimizing the environment for reciliation of the mucosa, h) speeding the growth or regrowth of cilia and i) delivering therapeutic agent(s) to the treatment site. Desirably the sealant will attach to a portion of the mucosa, cover other portions of the mucosa while leaving the cilia in such unattached portions free to undergo natural rhythmic cilia motion (viz., cilia beating).

The antimicrobial wash and optional sealant may desirably be used as a part of a multi-step treatment regimen which disrupts the bacteria or biofilm and discourages its return. For example, a series of steps that may be broadly classified as Cleansing/Disrupting/Killing; Protecting/Coating; Aerating; and Healing may be carried out. The Cleansing/Disrupting/Killing step may be carried out by administering the antimicrobial wash as described above. A separate antimicrobial agent also may be applied in a separate step after application of the antimicrobial wash and before application of the sealant. The Protecting/Coating step may be carried out by coating at least part of the thus-treated tissue with a protective sealant layer as described above. The Aerating step may be carried out by providing air passageways or improving air passageways to the treated tissues by opening occluded or partially occluded nasal passages, sinuses or sinus ostia. This may, for example, be accomplished by surgically removing obstructive tissue structures or by manually displacing such structures. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal sinus function. The disclosed method may advantageously be accomplished without requiring surgery, for example by applying the antimicrobial wash with sufficient power or pressure to remove, detach or otherwise disrupt the biofilm, removing the antimicrobial wash and applying the sealant through normal aspiration/suction techniques or by simple flushing of affected nasal passages without infusing the antimicrobial wash into or sealing into the more difficult to reach sinuses beyond the sinus ostia.

A comparable series of steps may be performed in a multi-step treatment regimen which disrupts bacteria or a biofilm in a portion of the middle or inner ear.

The invention is further illustrated in the following non-limiting examples.

EXAMPLE 1

The effectiveness of an antimicrobial wash at removing or reducing biofilms delivered with and without pressure or force was determined using an in vitro drip-flow reactor (DFR) system.

Bacterial isolates of S. aureus and P. aeruginosa were recovered from the sinuses of patients with sinus disorders. Patients with cystic fibrosis or an underlying immunosuppressive disease (HIV infection, insulin-dependent diabetes mellitus, or renal disease) and patients who had taken antibiotics or oral prednisone in the previous month were excluded. All patients had refractory sinusitis, namely, persistent symptoms resistant to medical therapy despite having undergone technically successful functional endoscopic sinus surgery (FESS) for refractory chronic rhinosinusitis (CRS) with or without nasal polyposis. The occurrence of CRS was diagnosed in accordance with the 2003 American Academy of Otolaryngology-Head and Neck Surgery (AAO-HNS) guidelines set out in Benninger et al., "Adult chronic rhinosinusitis: Definitions, diagnosis, epidemiology, and pathophysiology", Otolaryngol Head Neck Surg 129 (3 suppl): S1-S32 (2003). The selected patients had been refractory to medical therapy for more than 12 months before sample collection, and the failure of FESS was judged not to be associated with technical factors such as obstructive synechiae, frontal sinus obstruction, or a retained uncinate process. Samples were collected consecutively until 10 specimens each of S. aureus and P. aeruginosa were obtained using direct endoscopic guidance and the procedure described by Nadel et al., "Endoscopically guided cultures in chronic sinusitis". Am J Rhinol 12: 233-241 (1998). Briefly, a topical anesthetic agent was administered, the nasal ala was retracted, and an endoscope was used to visualize the middle meatus and sinus cavities. A thin, flexible calcium alginate swab (STARSWAB II™ Collection and Transport System, Starplex Scientific, Etobicoke, Ontario) was inserted and directed to the site with the most purulence. If no purulence was observed, the maxillary sinus surface was swabbed for 15 seconds. Care was taken to avoid contact with the lateral nasal wall or nasal vestibule.

Samples were plated and incubated using standard procedures. Bacteria were identified using a VITEK2™ system (Biomerieux, Durham, N.C.), Crystal violet staining to confirm the presence of biofilms was performed according to the method described by Stepanovic et al., "A modified microliter-plate test for quantification of staphylococcal biofilm formation", J Microbiol Methods 40: 175-179 (2000). For incubation and culture, previously frozen strains were inoculated on trypticase soy agar (TSA) with 0.5% sheep blood. After 24 hours, one to four colonies per strain were cultured on TSA. Cultures were incubated at 37° C. for 24 hours to condition them to a trypticase soy broth (TSB)-TSA medium and ensure noncontamination. Colonies grown on TSA solid medium were then amplified in 5 mL of TSB medium with 0.5% glucose according to the method described by Gotz, "Staphylococcus and biofilms", Mol Microbiol 43: 1367-1378 (2002) and incubated at 37° C. for at least 24 hours.

A DFR was used to determine the effectiveness of various test solutions delivered to S. aureus and P. aeruginosa biofilms on hydroxyapatite (HA)-coated microscope slides for removing these biofilms with and without pressure or force. The slides in the DFR are tipped at 10° from the horizontal, thereby modeling a low shear environment. The DFR was housed in an incubator at 37° C. under aerobic conditions. Approximately 20 minutes before bacterial inoculation, sterile medium (10% TSB for aureus; 1% TSB for P. aeruginosa) was dripped on the slides in the DFR and allowed to collect over the slides to form a conditioning layer. The slides were then inoculated with 1 mL of a culture of either S. aureus or P. aeruginosa. The DFR was returned to the horizontal so that the slides would be horizontal for 4 hours to allow bacterial attachment to the substrate.

Subsequently, the DFR was set so that the slides were once again at a 10° angle, with sterile medium dripping on the slides at a rate of 10 mL per hour. After 3 days, biofilm-removal experiments were performed. Two methods were used to treat the biofilms formed by each bacterial species. The first application method involved a static treatment in the DFR, with an antimicrobial solution (0.05 wt % PHMB, average molecular weight of 2,629, in 0.9 wt % saline solution, referred to as PHMB static) being dripped onto the biofilms. The second application method involved delivery outside the DFR of 0.9 wt % saline or different test formulations as shown in Table 1, using pressure to apply a hydrodynamic shearing force to the biofilm. For all treatments, preliminary runs were done to ensure that variations among slides were within acceptable limits. In addition, multiple plates of both bacterial species were produced to determine the within-run and run-to-run variations. A control slide with no treatment was made for each DFR run.

For static treatment, flow to the DFR was halted, the DFR was placed in a horizontal position, and the cover was removed. A 25 mL portion of PHMB static was applied to one slide. Control slides for PHMB static were treated using 0.9 wt % saline. After 10 minutes, the slides were rinsed with 0.9 wt % saline (25 mL). The DFR was then disconnected from the inflow tube, and each slide was removed under a laminar flow hood and placed in a sterile 50-mL tube. After another saline rinse (2 mL), the surface of the slide was scraped repeatedly, and the scrapings and saline were collected in the tube. The tube was vortexed for 10 seconds, sonicated for 2 minutes, and vortexed again for 10 seconds to disperse the bacteria into suspension. The suspensions were then serially diluted and 100-µL aliquots applied to three plates containing TSA and incubated at 37° C. for 24 hours. Colony-forming units (CFUs) were counted manually, and the number of CFUs per square centimeter was calculated. The resulting plate counts were log (10).

For hydrodynamic (pressure wash) treatment, the slides were removed from the DFR and placed in a glove box. The slides were placed in a holder and sprayed for approximately 10 seconds with either saline, or test formulations shown in Table 1 using a device that provided pressurized wash. Applied pressure was 31.4 psi with a flow rate of 5.5 mL/s, delivered via a nozzle with a 0.03-inch diameter at distances from 2.54 mm to 25.4 mm. The spraying was done with both a side-to-side and an up-and-down sweeping motion so that all areas were sprayed twice, once in each axis. The slides were then placed in sterile 50-mL tubes, rinsed, scraped, dispersed, incubated and evaluated as described above.

The mean (±SD) percent reduction from control values in the quantity of *S. aureus* and *P. aeruginosa* bacteria (viz., the number of CFUs on each plate) after each treatment was calculated and the results assessed using two-sample t tests (MINITAB™ version 14, Minitab, State College, Pa.). A P value less than 0.05 was considered to represent a significant difference from the control value. The results are shown below in Table 1, expressed as the mean number of colony-forming units per centimeter (log) derived from three plates assessed twice:

TABLE 1

Biofilm Log Reduction

| Run No. | Formulation | With Pressure | S. aureus | P. aeruginosa |
|---|---|---|---|---|
| 1 | 0.025 wt % PHMB in 0.9 wt % saline solution | Yes | 2.89 | 1.73 |
| 2 | 0.05 wt % PHMB in 0.9% saline | Yes | 3.01 | 2.62 |
| 3 | 0.1 wt % PHMB in 0.9% saline | Yes | 3.41 | 3.00 |
| 4 | 0.1 wt % PHMB + 1% glycerol in 0.9 wt % saline | Yes | 3.42 | 2.93 |
| 5 | 0.1 wt % PHMB + 1 wt % glycerol + 1 wt % surfactant (PLURONIC ™) in 0.9 wt % saline | Yes | 3.16 | 2.66 |
| 6 | 0.9 wt % saline | Yes | 2.32 | 1.42 |
| 7 | 0.05 wt % PHMB in 0.9 wt % saline solution | No (static) | 0.03 | 0.05 |

The results in Table 1 show that significant bacterial biofilm removal was obtained. Before treatment, biofilms formed in the DFR cultures of both *S. aureus* and *P. aeruginosa*, with CFU counts for these controls ranging from 9.21 log $CFU/cm^2$ for *P. aeruginosa* and 9.03 log $CFU/cm^2$ for *S. aureus*. Static administration of PI 1M B static (Run No. 7) resulted in a 0.03 log reduction (9.03 to 9.00 log $CFU/cm^2$) in the number of *S. aureus* CFUs and a 0.05 log reduction (9.21 to 9.16 log $CFU/cm^2$) in the number of *P. aeruginosa* CFUs. Mechanical disruption using hydrodynamic saline delivery alone (Run No. 6) decreased the number of *S. aureus* CFUs by 2.32 log units (9.59 to 7.26 log $CFU/cm^2$) and the number of *P. aeruginosa* CFUs by 1.42 log units (9.41 to 7.99 log $CFU/cm^2$). However, mechanical disruption using hydrodynamic 0.05% PHMB (Run No. 2) decreased the *S. aureus* CFU count by 3.01 log units (9.58 to 6.57 log $CFU/cm^2$) and the *P. aeruginosa* CFU count by 2.62 log units (9.41 to 6.78 log $CFU/cm^2$).

Of the test formulations investigated, the antimicrobial wash applied with pressure and using 0.1 wt % PHMB (Run No. 3) was the most effective in disrupting the bacterial biofilms. The antimicrobial wash using 0.9 wt % saline (Run No. 6) had appreciable biofilm-reducing effects. However, the presence of PHMB in the antimicrobial wash (Run Nos. 1, 2 and 3) significantly enhanced the reduction in CFU count in both *S. aureus* and *P. aeruginosa* biofilms. Large, statistically significant reductions occurred for 0.1% PHMB formulation, with the mean decreases in bacterial plate counts being 3.41 and 3.00 log (a reduction of 2,570 and 1,000 times), respectively, for *S. aureus* and *P. aeruginosa* biofilms. The addition of glycerol and surfactant did not significantly affect the biofilm reduction.

A decrease of this magnitude in vitro with only PHMB indicates that an appropriate in vivo treatment in the nasal cavities, sinus cavities, middle or inner ear should effectively disrupt bacterial biofilms found there. Any remaining low level of persistent bacterial infection might be dealt with by host defenses or a topically or orally administered antimicrobial agent, and by application of a sealant as described above.

EXAMPLE 2

Cytotoxicity

Formulations containing 0.025 wt %, 0.05 wt %, 0.1 wt %, 0.5 wt % PHMB with an average molecular weight of 2,629 were prepared in 0.9% saline and filtered through a 0.22 µm membrane. They were evaluated for potential cytotoxic effects following the guidelines of ISO10993-5, Biological Evaluation of Medical Devices—Part 5: Tests for in vitro Cytotoxicity. A negative control (high density polyethylene) and reagent control (0.9% sodium chloride) and a positive control (natural rubber latex, zinc carbamate accelerators, zinc oxide and titanium dioxide) was extracted in single strength MEM (1×MEM) at 37° C. for 24 hours. A mammalian cell culture monolayer having L-929 mouse fibroblast cells was incubated at 37° C. in the presence of 5% $CO_2$.

Following incubation, the monolayers were prepared with agarose and 2×MEM. The agarose was allowed to solidify over the cells to form the agarose overlay. Triplicates of filter discs of the antimicrobial wash and the three controls were each placed on the solidified agarose surface and incubated at 37° C. in the presence of 5% $CO_2$ for 24 hours. Following incubation, the cells were examined microscopically (100×) for cell decolonization around the test article and controls to determine the zone of cell lysis, if any.

To score for cytotoxicity, the following criteria shown in Table 2 were used:

TABLE 2

| Grade | Reactivity | Conditions of all Cultures |
|---|---|---|
| 0 | None | No detectable zone around or under specimen |
| 1 | Slight | Some malformed or degenerated cells under specimen |
| 2 | Mild | Zone limited to area under specimen |
| 3 | Moderate | Zone extending specimen size up to 10 mm |
| 4 | Severe | Zone extending farther than 1 cm beyond specimen |

Below are the results for the different wash solutions.

TABLE 3

| Run Nos. | Samples | Zone of Lysis (mm) | Grade | Reactivity |
|---|---|---|---|---|
| 1 | 0.025 wt % PHMB | 0 | 2 | Mild |
| 2 | 0.05 wt % PHMB | 1 | 3 | Moderate |
| 3 | 0.1 wt % PHMB | 2 | 3 | Moderate |
| 8 | 0.5 wt % PHMB | 6 | 3 | Moderate |
| 9 | Saline Control | 0 | 0 | None |
| 10 | Negative Control (high density polyethylene) | 0 | 0 | None |
| 11 | Positive Control (natural rubber latex | 7 | 3 | Moderate |

The results show that the antimicrobial wash generally has mild to moderate reactivity to fibroblast cells and may be considered non or low cytotoxic with a cytotoxicity score of 3 or less.

EXAMPLE 3

Ciliotoxicity

Ciliary beat frequency (CBF) was used to analyze the ciliotoxicity of the test formulations. All formulations were prepared in 0.9 wt % saline and sterilized by gamma radiation. PHMB with an average molecular weight of 2,629 was used. Glycerol and PLURONIC™ were purchased from Aldrich. Ex vivo samples of sinonasal epithelium from BALB/c mice (8 to 10 weeks of age) were used. The specimens were harvested by a method described in (Kalid et al. Physiologic Alterations in the Murine Model After Nasal Fungal Antigenic Exposure, Otolaryngology 139: 695-701 (2008)). Once harvested, the explants were placed in the test formulations as shown in Table 4. Explants were placed in a glass perfusion chamber on a thermostatically controlled stage and held in place with a nylon grid (1.5 mm) whose outer frame is snapped into the inside of the perfusion chamber. The stage and perfusate were maintained at a temperature between 35.5° C. and 37° C. with a dual channel heater (Warner Inst, Hamden, Conn.). Images were visualized with a Leica DMLFSA microscope set on an air table (TMC, Peabody, Mass.) with a water immersion objective and differential interference contrast (DIC) optics (Leica Microsystems, Inc. Bannockburn, Ill.). Images were captured by a Model 500 Redlake Motion Pro highspeed monochrome digital video camera (DEL Imaging Systems, LLC, Cheshire, Con.). The digital image-sampling rate was set at 250 frames per second (fps). A three-second video was recorded at each time point. The video images were written to a PCI 2.2 board and then analyzed using Midas Professional Analyst video image processing software (XCitex, Cambridge, Mass.). Beating cilia were analyzed with the 1-D line-tracking algorithm included in the motion analysis software. After locating a region of beating cilia, an analysis grid was created by drawing a line across a segment of beating cilia. The software captured the motion history within the analysis grid for the duration of the video and recorded the gray-scale intensity variation as a function of time. This track history represented the oscillations of the cilia in the form of a time-based waveform graph. The principal frequency was determined with a customized subprogram in MatLab. The formulations that allow cilia beat after 10 minutes exposure are considered non-ciliotoxic.

TABLE 4

| Run Nos. | Formulations | Cilia beat after 10 minutes |
|---|---|---|
| 2 | 0.05 wt % PHMB | yes |
| 3 | 0.1 wt % PHMB | yes |
| 4 | 0.1 wt % PHMB + 1 wt % glycerol | yes |
| 5 | 0.1 wt % PHMB + 1 wt % glycerol + 1 wt % PLURONIC ™ | yes |
| 12 | 0.3 wt % PHMB | no |
| 13 | 0.3 wt % PHMB + 3 wt % glycerol | no |
| 14 | 0.3 wt % PHMB + 3 wt % glycerol + 3 wt % PLURONIC ™ | no |

The results show that the antimicrobial wash generally is non-ciliotoxic.

EXAMPLE 4

Sterilization

Run 1 (0.025% PHMB (average weight molecular weight of 2,629) in 0.9% saline) was used to explore different sterilization approaches including autoclave, filtration, gamma sterilization and E-beam in different packaging (glass vials, plastic syringes, IV bags or plastic bottles). Packaged solutions of PHMB before and after sterilization were analyzed for concentration changes as measured by UV spectrometer absorbance at 235 nm. A standard curve was established using a series of PHMB standard solutions.

Briefly, 1 mL solution (before and after sterilization) was diluted into 25 mL deionized water. UV absorption at 235 nm was measured using Spectrophotometer (Thermo Electron Corporation). Deionized water was used as blank.

TABLE 5

| Sterilization method | Container | Before sterilization (corrected absorption @ 235 nm) | After sterilization (corrected absorption @ 235 nm) | % Change |
|---|---|---|---|---|
| Autoclave (121° C. for 60 min) | plastic tube | 0.6 | 0.6 | +3.0% |
| Filtration (0.2 µm nylon filter) | plastic bag | 0.6 | 0.6 | −3.6% |
| Gamma (25.0 kGy to 67.7 kGy) | glass vial | 0.6 | 0.6 | −4.9% |
| E-beam (25 kGy) | plastic syringe | 0.6 | 0.6 | −7.9% |

The results indicated that after sterilization, PHMB concentration changes were within ±10%, indicating minimum damage to PHMB by autoclave, filtration, gamma and E-beam sterilizations.

EXAMPLE 5

Zone of Inhibition

Zone of inhibition (ZOI) test was used to investigate the antimicrobial property of PHMB solutions. All formulations were prepared in 0.9 wt % saline and sterilized by gamma radiation. PHMB with an average molecular weight of 2,629 was used. Samples were tested for ZOI against *Staphylococcus aureus* (ATCC No. 25923), *Staphylococcus epidermidis* (ATCC No. 12225), *Pseudomonas aeruginosa* (ATCC No. 10145), and *Escherichia coli* (ATCC No. 25922). Cultures were applied to Mueller-Hinton agar plates to create a lawn of bacteria, 6 mm blank paper discs were placed on the plates and 25 ul of the PHMB solutions were delivered to the discs. 0.9% saline was used as a control. The plates were incubated at 37° C. for 18 hours and then observed for zones of inhibition around the test discs. The term "zone of inhibition" denotes an area around the formulations where bacterial growth was inhibited. Results are shown in Table 6.

TABLE 6

| Run | Samples | *Staphylococcus aureus* | *Staphylococcus epidermidis* | *Pseudomonas aeruginosa* | *Escherichia coli* |
|---|---|---|---|---|---|
| 1 | 0.025 wt % PHMB | Zone | Zone | Zone | Zone |
| 2 | 0.05 wt % PHMB | Zone | Zone | Zone | Zone |
| 3 | 0.1 wt % PHMB | Zone | Zone | Zone | Zone |
| Control | 0.9% Saline | No zone | No zone | No zone | No zone |

The results show that the formulations were antimicrobial and produced zones of inhibition.

Some additional non-limiting embodiments are provided below to further exemplify the present invention.

1. A method for biofilm removal comprises;
   applying with pressure an antimicrobial wash to a bacterial biofilm attached or adhered to a surface of a human or animal tissue, or on an implant device; and
   detaching, removing or otherwise disrupting at least a part of the biofilm; wherein the antimicrobial wash consists essentially of a biguanide compound or mixtures thereof.
2. A method for biofilm removal comprises:
   applying with pressure an antimicrobial wash to a bacterial biofilm attached or adhered to a surface of a human or animal tissue, or on an implant device; and
   detaching, removing, or otherwise disrupting at least a part of the biofilm; wherein the antimicrobial wash consists of a biguanide compound or mixtures thereof.
3. A method for removing a biofilm comprising:
   applying with pressure an antimicrobial wash comprising a biguanide compound or mixtures thereof to a biofilm attached or adhered to a surface of a human or animal tissue, or on an implant device; and
   providing comparable or improved detachment, removal or disruption to at least a part of the biofilm compared to an antimicrobial wash that does contain a surfactant, a lubricating agent or wetting agent or combination thereof.
4. A method for treating rhinosinusitis and other bacterial sinus conditions, which method comprises:
   applying with pressure an antimicrobial wash comprising a biguanide compound or mixtures thereof to a treatment site within a nasal or sinus cavity; and
   detaching, removing or otherwise disrupting at least a part of the bacteria or a biofilm.
5. A method for treating rhinosinusitis and other bacterial sinus conditions, the method comprises:
   applying with pressure an antimicrobial wash to a treatment site; and
   detaching, removing or otherwise disrupting at least a part of the bacteria or a biofilm;
   wherein the antimicrobial wash consists essentially of a biguanide compound or mixtures thereof.
6. A method for treating rhinosinusitis and other bacterial sinus conditions, the method comprises:
   applying with pressure an antimicrobial wash to a treatment site; and
   detaching, removing or otherwise disrupting at least a part of the bacteria or a biofilm;
   wherein the antimicrobial wash consists of a biguanide compound or mixtures thereof
7. A method for treating rhinosinusitis and other bacterial sinus conditions, the method comprises:
   applying with pressure an antimicrobial wash comprising a biguanide
   detaching, removing or otherwise disrupting the bacteria to provide greater than 1-log order reduction in one or more of *Staphylococcus aureus, Pseudomonas aeruginosa, Staphylococcus epidermidis, Escherichia coli Staphylococcus pneumonia, Haemophilus influenzae* or *Moraxella catarrhalis* bacteria compared to an antimicrobial wash that contains a surfactant, a lubricating agent or wetting agent or combination thereof.
8. A method for treating otitis media and other bacterial ear conditions, which method comprises:
   applying with pressure an antimicrobial wash comprising a biguanide compound or mixtures thereof to a treatment site within an ear; and
   detaching, removing or otherwise disrupting at least a part of the bacteria or a biofilm.
9. A method for treating otitis media and other bacterial ear conditions, the method comprises:
   applying with pressure an antimicrobial wash to a treatment site; and
   detaching, removing or otherwise disrupting at least a part of the bacteria or a biofilm;
   wherein the antimicrobial wash consists essentially of a biguanide compound or mixtures thereof
10. A method for treating otitis media and other bacterial ear conditions, the method comprises:
    applying with pressure an antimicrobial wash to a treatment site;
    detaching, removing or otherwise disrupting at least a part of the bacteria or a biofilm;
    wherein the antimicrobial wash consists of a biguanide compound or mixtures thereof.
11. A method for treating otitis media, and other bacterial ear conditions, the method comprises:

applying with pressure an antimicrobial wash comprising a biguanide compound or mixtures thereof; and detaching, removing or otherwise disrupting the bacteria to provide greater than 1-log order reduction in one or more of *Staphylococcus aureus, Pseudomonas aeruginosa, Staphylococcus epidermidis, Escherichia coli Staphylococcus pneumonia, Haemophilus influenzae* or *Moraxella catarrhalis* bacteria compared to an antimicrobial wash that contains a surfactant, a lubricating agent or wetting agent or combination thereof.

12. A surfactant-free antimicrobial wash comprising a biguanide compound or mixtures thereof.

13. A composition for biofilm removal comprising an antimicrobial wash comprising a biguanide solution, wherein the antimicrobial wash does not contain a surfactant, lubricating agent, wetting agent or combination thereof.

14. A composition for biofilm removal comprising an antimicrobial wash comprising a biguanide solution, wherein the antimicrobial wash is non-ciliotoxic 15. A kit for treating rhinosinusitis and other bacterial sinus conditions comprising a device that can apply solution with pressure; the device containing an antimicrobial wash and printed instructions describing proper use of the kit, the antimicrobial wash comprising a biguanide solution.

16. A kit for treating otitis media and other bacterial ear conditions comprising a device that can apply solution with pressure: the device containing an antimicrobial wash and printed instructions describing proper use of the kit, the antimicrobial wash comprising a biguanide solution.

17. An apparatus for treating bacterial conditions comprising:
a spray device containing an antimicrobial solution comprising a biguanide solution, the spray device capable of applying the antimicrobial solution with pressure.

18. The embodiment 1-17 wherein the biguanide is a polybiguanide,

19. The embodiment 18 wherein the polybiguanide is a polyhexamethylene biguanide, salts thereof or combinations thereof.

20. The embodiment 1-19 wherein the biguanide is about 0.005 wt % to about 0.5 wt % of the total solution.

21. The embodiment 1-19 wherein the biguanide is about 0.025 wt % to about 0.2 wt % of the total solution.

22. The embodiment 1-21 wherein the polybiguanide is about 1,000 to about 50,000 weight average molecular weight.

23. The embodiment 1-22 wherein the pressure is about 30,000 Pascal to about 480,000 Pascal.

24. The embodiment 1-23 wherein the antimicrobial wash is non or low cytotoxic,

25. The embodiment 24 wherein the non or low cytotoxic is a cytotoxicity score of 3 or less as measured by ISO010993-5, Biological Evaluation of Medical Devices—Part 5.

26. The embodiment 1-25 wherein the antimicrobial wash is non-ciliotoxic.

27. The embodiment 1-26 wherein the antimicrobial wash is in sterile packaging,

28. The embodiment 1-27 wherein the sterile packaging is autoclave, electron-beam or gamma sterilized.

29. The embodiment 1-28 further applying a polymeric sealant to a treatment site, 30. The embodiment 15 and 16 wherein the device is a syringe, or pouch.

31. The embodiments 14-17 wherein the antimicrobial solution is delivered or applied to a nose, ear and throat.

Although specific embodiments have been illustrated and described herein. It will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the embodiments discussed herein. Therefore, it is manifestly intended that this invention be limited only by the claims and the equivalents thereof. All patents, patent applications and literature cited in the specification are hereby incorporated by reference in their entirety. In the case of any inconsistencies, the present disclosure, including any definitions herein will prevail.

We claim:

1. An apparatus comprising: a sinus irrigation system for treating bacterial sinus conditions, the sinus irrigation system containing an antimicrobial solution comprising a biguanide compound or mixtures thereof, wherein the antimicrobial solution is non-ciliotoxic, and wherein the sinus irrigation system applies the antimicrobial solution with pressure into a nasal or sinus cavity of a patient.

2. The apparatus according to claim 1, wherein the sinus irrigation system is configured to apply the antimicrobial solution at a pressure of about 30,000 Pascal to about 480,000 Pascal.

3. The apparatus according to claim 1, wherein the biguanide compound is a polybiguanide.

4. The apparatus according to claim 3, wherein the polybiguanide is a polyhexamethylenebiguanide, a polyhexamethylenebiguanide salt or combination thereof.

5. The apparatus according to claim 1, wherein the biguanide compound is about 0.005 wt % to about 0.5 wt % of the antimicrobial solution.

6. The apparatus according to claim 1, wherein the biguanide compound is about 0.025 wt % to about 0.2 wt % of the antimicrobial solution.

7. The apparatus according to claim 1, wherein the antimicrobial solution has a cytotoxicity score of 3 or less as measured by ISO10993-5, Biological Evaluation of Medical Devices—Part 5.

8. The apparatus according to claim 1, wherein the antimicrobial solution is substantially free of surfactants and wetting agents.

9. A kit for treating bacterial sinus conditions comprising:
the apparatus of claim 1; and
printed instructions describing proper use of the kit.

* * * * *